United States Patent [19]
Goldstein

[11] 4,077,949
[45] Mar. 7, 1978

[54] POLYPEPTIDE HORMONES OF THE THYMUS

[75] Inventor: Gideon Goldstein, Short Hills, N.J.

[73] Assignee: Sloan-Kettering Institute for Cancer Research, New York, N.Y.

[21] Appl. No.: 606,843

[22] Filed: Aug. 22, 1975

Related U.S. Application Data

[63] Continuation-in-part of Ser. No. 429,202, Dec. 28, 1973, abandoned.

[51] Int. Cl.$^2$ ..................... C07C 103/52; A61K 37/00
[52] U.S. Cl. .............................. 260/112.5 R; 424/177
[58] Field of Search .................... 260/112.5 R, 112 R; 424/177

[56] References Cited

FOREIGN PATENT DOCUMENTS 1,195,980 6/1970 United Kingdom.

OTHER PUBLICATIONS

Goldstein et al.: Annals N. Y. Acad. Sci., 183, 230–240 (1971).
Goldstein: Triangle, 11, 7–14 (1972).
Goldstein: The Lancet, 119–122 (July 20, 1968).

*Primary Examiner*—Delbert R. Phillips
*Attorney, Agent, or Firm*—Lowe, King, Price & Markva

[57] ABSTRACT

There are disclosed closely related new polypeptides isolated from bovine thymus, which are distinct polypeptides denoted as Thymin I and Thymin II or Thymopoietin I and Thymopoietin II, respectively. Thymin I may be characterized as having a relative mobility (Rf) on 7% polyacrylamide gel disc electrophoresis of 0.63 with respect to methyl green at a pH of 4.3, and having the following structural sequence:

$H_2$N-GLY-GLN-PHE-LEU-GLU-ASP-PRO-SER-VAL-LEU-THR-LYS-GLU-LYS-LEU-LYS-SER-GLU-LEU-VAL-ALA-ASN-ASN-VAL-THR-LEU-PRO-ALA-GLY-GLU-GLN-ARG-LYS-ASP-VAL-TYR-VAL-GLN-LEU-TYR-LEU-GLN-HIS-LEU-THR-ALA-VAL-LYS-ARG-COOH.

Thymin II may be characterized as having a relative mobility (Rf) on 7% polyacrylamide gel disc electrophoresis of 0.57 with respect to methyl green at a pH of 4.3, and having the following structural sequence:

$H_2$N-SER-GLN-PHE-LEU-GLU-ASP-PRO-SER-VAL-LEU-THR-LYS-GLU-LYS-LEU-LYS-SER-GLU-LEU-VAL-ALA-ASN-VAL-THR-LEU-PRO-ALA-GLY-GLU-GLN-ARG-LYS-ASP-VAL-TYR-VAL-GLN-LEU-TYR-LEU-GLN-THR-LEU-THR-ALA-VAL-LYS-ARG-COOH.

Both polypeptides are highly purified and in powder form and are isolated from bovine thymus by multiple purification methods involving molecular sieving and chromatography. Both products cause delayed impairment of neuromuscular transmission in vivo and induce bone marrow cells to develop the characteristics of thymus-derived lymphocytes and thus are useful in therapeutic areas involving thymic or immunity deficiencies or imbalances, and neuromuscular hyperactivity.

8 Claims, 8 Drawing Figures

FIG. 1
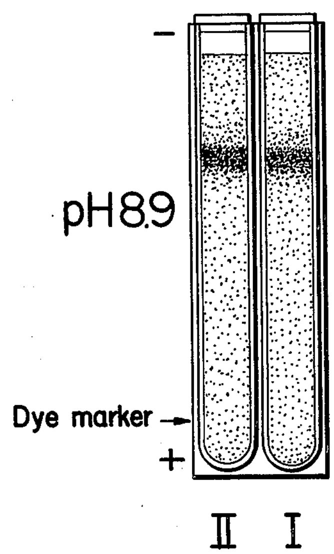
FIG. 2
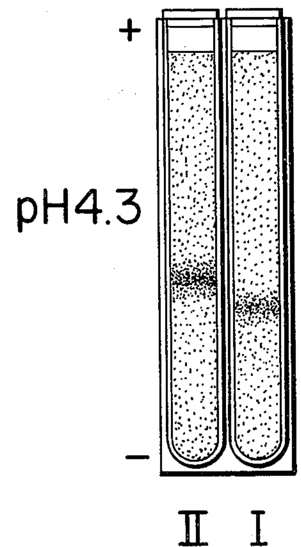
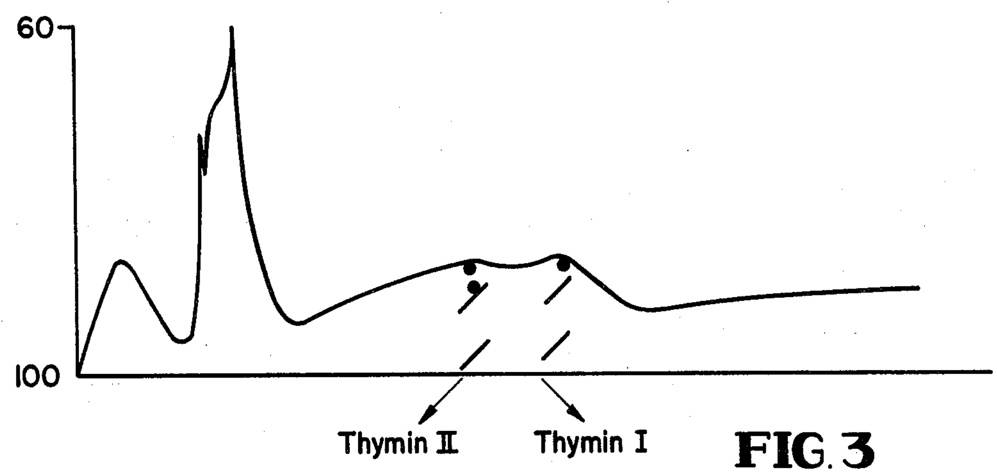
FIG. 3
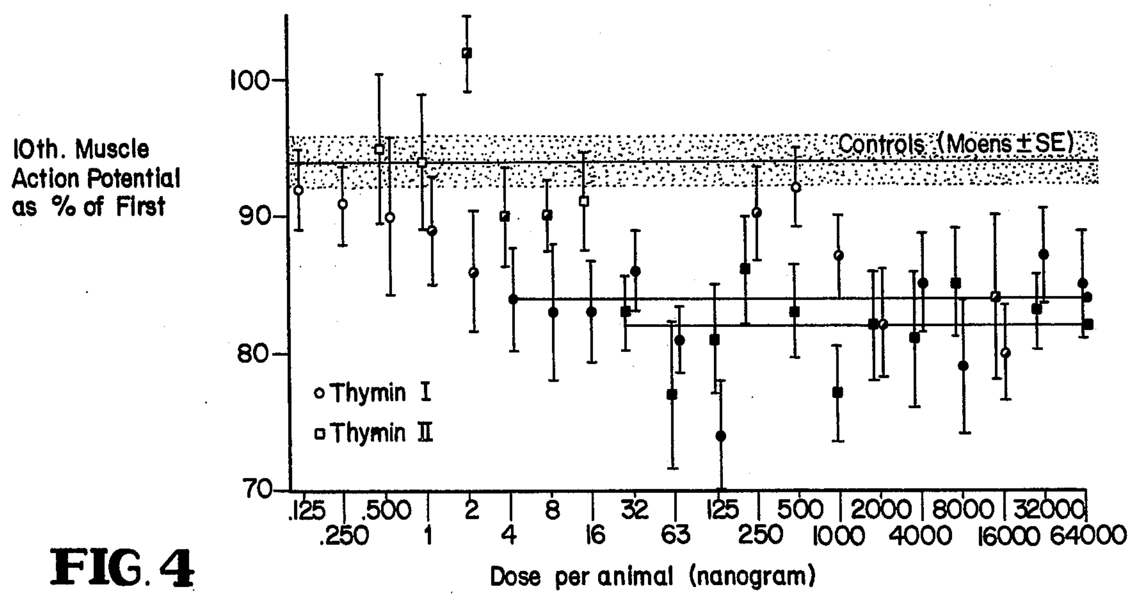
FIG. 4

NUMBER OF CELLS ADDED TO INHIBIT CYTOTOXIC ANTIBODY ($x10^{-4}$)

POLYPEPTIDE HORMONES OF THE THYMUS

The invention described herein was made in the course of work under a grant or award from the Department of Health, Education and Welfare.

CROSS-REFERENCE TO RELATED APPLICATIONS

This is a continuation-in-part of my copending application Ser. No. 429,202, filed Dec. 28, 1973 now abandoned.

BACKGROUND OF THE INVENTION

1. Field of the Invention

This invention relates generally to new polypeptides and more particularly to closely related new polypeptides isolated in purified form from the bovine thymus, to methods for isolation of these new polypeptides, and therapeutic fields of use for the polypeptides.

2. Description of the Prior Art

It is well known that polypeptides have been isolated from various organs or animals. Until about the past decade, however, very little was known about the thymus, an organ which in man comprises about 0.8% of his body weight at birth, although it has been previously hypothesized that a neuromuscular blocking substance existed in the thymus. Despite keen interest in possible functions of the thymus and early speculation and experimentation, little was known of the function of the thymus until recently. It is now realized, however, that the thymus is a compound organ with both epithelial (endocrine) and lymphoid (immunological) components and thus the thymus is involved in the immunity functions of the body. The thymus is known to be a compound organ consisting of an epithelial stroma derived from the third branchial arch and lymphocytes derived from stem cells originating in haemopoietic tissues, Goldstein et al., *The Human Thymus,* Heinemann, London, 1969. Lymphocytes are differentiated within the thymus and leave as mature thymus-derived cells, called T cells, which circulate to the blood, lymph, spleen and lymph nodes. The induction of stem cell differentiation within the thymus appears to be mediated by secretions of the epithelial cells of the thymus but difficulties with bioassays have hindered the complete isolation and structural characterization of any hormones which may be present.

It has been known for some time that the thymus is connected with the immunity characteristics of the body and therefore great interest has been indicated in substances which have been isolated from the thymus. In this regard, there have been published in recent years a relatively large body of articles based on scientific work relating to materials which are present in bovine thymus. In fact, the Applicant has published a number of articles which relate to his research in this area. Pertinent publications may be found for example in *The Lancet,* July 20, 1968, pps. 119–122; *Triangle,* Vol. 11, No. 1, pps. 7–14, 1972; *Annals of the New York Academy of Sciences,* Vol. 183, pps. 230–240, 1971; and *Clinical and Experimental Immunology,* Vol. 4, No. 2, pps. 181–189, 1969.

In the article by Goldstein and Manganaro in *Annals of the New York Academy of Sciences,* Vol. 183, pps. 230–240, 1971, there are disclosures regarding the presence of a thymic polypeptide which causes a myasthenic neuromuscular block in animals, which is analogous to the human disease of myasthenia gravis. Further, in this article it was discovered that two distinct effects were caused by separate polypeptides in bovine thymus. One of these polypeptides, named "thymotoxin", was believed to cause myositis but it was further indicated that this polypeptide had not been isolated although it appeared to be a polypeptide of approximately 7,000 molecular weight, had a strong net positive charge and was reatined on CM-Sephadex at a pH of 8.0.

It was further disclosed that small amounts of a material named "thymin" had been detected in bovine thymus using saline extraction, heat treatments, centrifugation, ion exchange chromatography, molecular sieving on Sephadex, hydroxyl apatite chromatography and preparative polyacrylamide electrophoresis. At page 235, it was indicated that neuromuscular blocking activity had been detected in a polypeptide fraction of approximately 7,000 molecular weight and that doses of 0.2 milligram of this material injected subcutaneously in 200 gram rats caused myasthenic neuromuscular block at five days as demonstrated by electromyography. The polypeptides of the present invention are not disclosed by these prior art disclosures.

It will be apparent from the above articles and the various publications which are cited in these articles that a large amount of work has been done in the isolation and identification of materials from bovine thymus. However, in none of these articles has there been disclosed the isolation of pure materials which are highly pure polypeptides whch can now be characterized by definite chemical and physical properties and which have been isolated in a form which did not exist in the bovine thymus from where they were obtained. Further, the new polypeptides isolated from bovine thymus in accordance with this invention exhibit physiological characteristics which suggest that they are important to medical science in the study of the immunity system of the human body and have many therapeutic applications.

SUMMARY OF THE INVENTION

It is accordingly one object of this invention to provide new polypeptides which are important biologically.

A further object of the invention is to provide new polypeptides identified as Thymin I and Thymin II, now named as Thymopoietin I and Thymopoietin II, which have activity in impairing neuromuscular transmissions detectable by electromyography and induce differentiation of bone marrow cells to T cells thus giving rise to thymus-derived lymphocytes and thereby being highly useful in the immunity system of humans and animals.

A further object of the invention is to provide methods for isolating and separating the novel polypeptides of this invention, as well as compositions and metods for their use in biological actions.

Other objects and advantages of the invention will become apparent as the description thereof proceeds.

In satisfaction of the foregoing objects and advantages there are provided by this invention highly pure polypeptides obtained from bovine thymus, which polypeptides are characterized as Thymin I and Thymin II, now named as Thymopoietin I and Thymopoietin II, Thymopoietin I being isolated as a powder separate from Thymopoietin II; Thymopoietin I having a relative mobility (Rf) of 0.63 with respect to methyl green at a pH of 4.3 and a relative mobility (Rf) of 0.30 with respect to bromphenol blue at a pH of 8.9; Thymopoietin II having a relative mobility (Rf) of 0.57 at a pH of 4.3 with respect to methyl green and a relative mobility (Rf) of 0.30 at a pH of 8.9 with respect to bromphenol blue. All relative mobilities are on 7% polyacrylamide disc electrophoresis. These polypeptides are isolated from bovine thymus by a series of steps involving homogenizing in saline solution, heating, centrifuging, membrane and molecular sieve separations, adsorption chromatography, ion exchange chromatography with final desalting by molecular sieve chromatography and lyophilization. The Thymopoietin products are useful in many areas and are particularly characterized by their ability in subanogram concentrations to induce bone marrow cells to develop the characteristics of intrathymic lymphocytes and thus are of assistance in the immunity functions of the body.

BRIEF DESCRIPTION OF THE DRAWING

Reference is now made to the drawing accompanying this application wherein:

FIG. 1 shows a polyacrylamide gel from disc electrophoresis of Thymin I and Thymin II at a pH of 8.9 and shows the major band present;

FIG. 2 shows a polyacrylamide gel from disc electrophoresis of Thymin I and Thymin II at a pH of 4.3 and shows the major bands present;

FIG. 3 is a chart which shows the peaks of Thymin I and Thymin II as measured by ultraviolet absorbence as recovered from bovine thymus;

FIG. 4 is a chart showing the electromyographic response of mice to supramaximal nerve stimulation by Thymin I and Thymin II;

DESCRIPTION OF PREFERRED EMBODIMENTS

Figure 5:
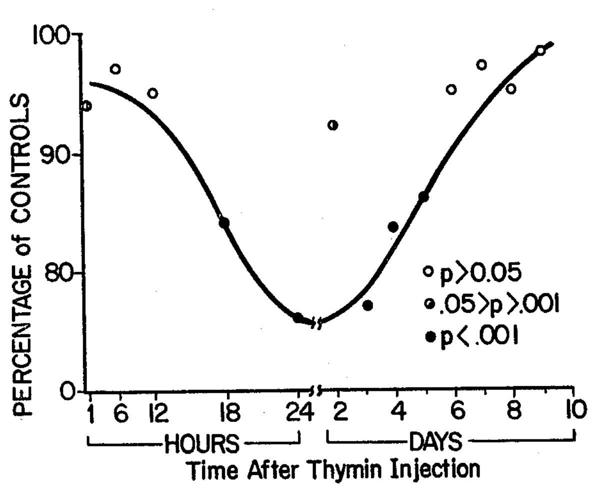
FIG. 5 is a chart showing the electromyographic response of mice at various times after a single injection of Thymin I expressed as a percentage of the response of mice injected with solvent alone.

As indicated above, this invention is concerned with two closely related polypeptides which have been isolated from the thymus of bovine by their effect in causing a delayed impairment of neuromuscular transmission in vivo.

In parent application Ser. No. 429,202, the products were named as Thymin I and Thymin II. However, because of the possible confusion of these products with other substances of the art and with the pyrimidine base "thymine", the products of this invention are now named as "Thympoietin I" and "Thymopoietin II" and will be referred to by these names hereinafter. In addition, at the time of filing the parent application the amino acid sequence of these products were not known. The structural formulae have now been determined.

This invention is also concerned with the methods for isolation of these new polypeptides, methods for their purification and methods for use in taking advantage of their biological activities.

As indicated above, the hypothesis of a neuromuscular blocking substance in thymus is not novel. It was proposed in the 1940's in relation to the then current concepts of the curare-like nature of the myasthenic neuromuscular block, the known association of thymic pathology with the disease and the empirical discovery that thymectomy was an effective treatment for myasthenia gravis. Despite the large amount of work in this area, an unequivocal demonstration of such a neuromuscular blocking substance was not obtained. Although no consistent acute effects of thymus extract could be demonstrated, it was found that when thymus extracts were injected into animals, an impairment of neuromuscular transmission could be detected after a delay of several days. This effect of a delayed production of impairment of neuromuscular transmission has served as a bioassay for monitoring the chemical fractionation of chemical extracts obtained from bovine thymus.

This approach to the isolation of thymic hormones was developed from experimental studies related to the human disease myasthenia gravis. Myasthenia gravis is characterized by a deficit in neuromuscular transmission and an associated thymic pathology has long been recognized in this disease. A study of clinical, pathological and immunological features of myasthenia gravis led to the hypothesis that autoimmune disease of the thymic is the lesion basic to this disease. A laboratory animal model of experimental autoimmune thymitis was developed and these animals were shown to have an abnormality of neuromuscular transmission similar to that of myasthenia gravis by a number of criteria. Experimental analysis of this laboratory model revealed that the effect on neuromuscular transmission was mediated by a substance released from the diseased thymus and neurophysiological studies in thymectomized and thymus grafted animals suggested that this substance was secreted physiologically.

This application discloses the isolation of two highly purified closely related polypeptides from bovine thymus which exhibit similar effects on neuromuscular transmission. Thus, these extracts produce, after a single injection of 4 to 32 nanogram per mouse, an impairment of neuromuscular transmission detectable by electromyography at 1 to 5 days following injection. It was also found that these purified polypeptides induce differentiation of bone marrow cells to T cells and thus appear to be thymic hormones which induce differentiation of the lymphopoietic stem cells which give rise to thymus derived lymphocytes or T cells.

The two polypeptides isolated in accordance with this invention are denoted herein as Thymopoietin I and Thymopoietin II. They are high purity powders which have been isolated from bovine thymus extracts and which have not been known heretofore. Further, Thymopoietin I and Thymopoietin II have been isolated from each other and exist in a form not known heretofore. In the thymus it seems clear that they existed only in admixture and in fact may have been present in unknown admixture in the impure material described as "Thymin" in *Annals of New York Academy of Sciences,* Vol. 183, pps. 230–240, 1971. The polypeptides of this invention are considered distinct from the material disclosed heretofore as "Thymin". Further the polypeptides of this invention are of greater purity than the prior material, exist in a physical form not detectable heretofore and exhibit far greater biological acitivites. The present application also provides procedures for isolation of the mixture from bovine thymus and separation of this mixture to produce Thymopoietin I and Thymopoietin II.

Thymopoietin I has been determined to be a polypeptide which has the following structural sequence or formula:

$H_2$-GLY-GLN-PHE-LEU-GLU-ASP-PRO-SER-VAL-LEU-THR-LYS-GLU-LYS-LEU-LYS-SER-GLU-LEU-VAL-ALA-ASN-ASN-VAL-THR-LEU-PRO-ALA-GLY-GLU-GLN-ARG-LYS-ASP-VAL-TYR-VAL-GLN-LEU-TYR-LEU-GLN-HIS-LEU-THR-ALA-VAL-LYS-ARG-COOH.

Thymopoietin II has been determined to be a polypeptide which has the following structural sequence or formula:

$H_2N$-SER-GLN-PHE-LEU-GLU-ASP-PRO-SER-VAL-LEU-THR-LYS-GLU-LYS-LEU-LYS-SER-GLU-LEU-VAL-ALA-ASN-ASN-VAL-THR-LEU-PRO-ALA-GLY-GLU-GLN-ARG-LYS-ASP-VAL-TYR-VAL-GLN-LEU-TYR-LEU-GLN-THR-LEU-THR-ALA-VAL-LYS-ARG-COOH.

As may be noted, Thymopoietin II differs from Thymopoietin I by replacement of Gly with Ser in position (1) and Thr with His in position (43).

In the above structures, the amino acid components of the peptides are identified by abbreviation for convenience. These abbreviations are as follows:

| Amino Acid | Abbreviated Designation |
|---|---|
| L-arginine | ARG |
| L-Alanine | ALA |
| L-glutamine | GLN |
| L-aspartic acid | ASP |
| L-glutamic acid | GLU |
| L-histidine | HIS |
| L-proline | PRO |
| L-lysine | LYS |
| Glycine | GLY |
| L-leucine | LEU |
| L-phenylalanine | PHE |
| L-asparagine | ASN |
| L-serine | SER |
| L-tyrosine | TYR |
| L-threonine | THR |
| L-valine | VAL |

Both Thymopoietin I and Thymopoietin II exhibit neuromuscular blocking activity and were found associated with material which strained with Coomassie blue, and had relative mobilities (RF) of about 0.30 with respect to bromphenol blue at a pH of 8.9 on 7% polyacrylamide gel disc electrophoresis. The relative mobilities of Thymopoietin I and Thymopoietin II are shown in FIGS. 1 and 2 which illustrate the results obtained from polyacrylamide disc electrophoresis and also indicate the high purity of the materials. In FIG. 1, the polyacrylamide gels from disc electrophoresis of 200 microgram samples of Thymin I and Thymin II are shown when conducted at a pH of 8.9. The gels were fixed with trichloroacetic acid and then stained with Coomassie blue. One major band is present in each gel. At a pH of 8.9 Thymin I or Thymopoietin I appears to migrate slightly faster than Thymin II or Thymopoietin II, but the mobilities are not clearly distinguishable. Therefore, it was determined that both products have substantially similar relative mobilities at a pH of 8.9.

A clear distinction between the products is shown in FIG. 2 however, which shows the results of polyacrylamide disc electrophoresis conducted at a pH of 4.3. Again the gels were fixed with trichloroacetic acid. At this pH, as may be seen in FIG. 2, Thymin I or Thymopoietin I was shown to have a relative mobility of 0.63 with respect to methyl green whereas Thymin II or Thymopoietin II at a pH of 4.3, had a relative mobility of 0.57. Thus, at a pH of 4.3 it is very clear that Thymin I migrates distinctly faster than Thymin II and, since these mobilities have been found to remain consistent and they do not interconvert, it is clear that the products are distinct and separate polypeptides.

The purification procedures were monitored by analytical polyacrylamide disc electrophoresis. Seven percent polyacrylamide gels were run at pH 8.9 and pH 4.3. Methyl green was used as a dye marker in the acid gels run towards the cathode and bromphenol blue was used in the basic gels run towards the anode. Spacer gels were not used, the samples being loaded in electrode buffer made up with the dye marker in 25% sucrose. The gels were fixed in 12.5% trichloracetic acid, stained with Coomassie blue and the relative mobilities (Rf) were calculated with respect to the dye markers.

Thymin I (Thymopoietin I) and Thymin II (Thymopoietin II) are obtained from bovine thymus by a series of steps involving intricate purification and separation. Generally, the process involves obtaining fresh clean disected bovine thymus which has been stored at temperatures of less than 0° C., i.e., about −30° to −10° C. In conducting the process, a batch of the thymus is initially homogenized with about 20–30 weight per volume of a buffered saline solution and good mixture obtained to the point of homogenization by the presence of agitation. The buffered saline may include any of the well known solutions which are used for this purpose including sodium and potassium phosphate buffered salt solutions and in general, any of the alkali metal or ammonium salt solutions and should have a concentration of about 0.005 M to .2 M. A particularly preferred solution is an ammonium bicarbonate aqueous solution. The resulting homogenized extract is then heated at a temperature of about 60°–90° C. for 15 minutes up to about 1 hour depending on the temperature used in order to homogenize the mixture as much as possible. Thereafter, any nonhomogenized material is removed by any suitable method, e.g. high speed centrifugation, for one-fourth hour to about 1 hour. The resulting supernatant is then filtered in order to remove any insoluble materials and since the remaining steps are usually carried out at room temperature, it may be necessary to add a commercial bacteriostat to the mixture at this point in order to prevent contamination. If the process were carried out in a cold room or at low temperatures, for example around 4° C., the bacteriostatic agent may be omitted.

The resulting mixture is then separated according to molecular size, preferably with the use of membranes in order to separate materials present in the mixture on the basis of size. The purpose of this separation is to use a membrane which will permit the Thymin compounds to pass through the membrane while holding up larger molecular weight materials. As indicated, since the Thymin compounds have molecular weights around 6,000 to 7,000 it is sufficient for purposes of this step to prevent passage through the membrane of any material which would have molecular weights of, for example about about 100,00 dalton. Membranes and methods are well known in the art which will affect this separation.

After this step, the solution which passed through the (dialysate) membrane, which contains the desired products, is then subjected to further enrichment on the basis of molecular size by passing the extract through a membrane under dialysis conditions which will prevent the higher molecular weight materials from passing through but permits the smaller molecular weight materials present in the extract to pass through the membrane. Thus, in this step, materials having molecular weights in the range of 2,000 to 100,00 dalton are prevented from passing through the membrane by selection of a membrane for this purpose in accordance with known procedures while permitting materials of smaller molecular weight to pass through.

In this step of the procedure a major reduction in volume is obtained in that after completion of this dialysis the volume of the extract is reduced so that less than 1% by volume of the extract is retained for the next step.

The resulting retentate is then fractionated by molecular exclusion chromatography using molecular sieves to effect the fractionation. In this step, a molecular sieve is used for the chromatography operation which has a pore size such that materials having molecular weight above about 30,000 are totally excluded from the pores and pass through the chromatographic column rapidly. The pore size is also selected so that materials having a molecular weight of less than about 1,500 will be totally permeable within the pores and will be fully retarded on the column. A molecular sieve which is very suitable to this purpose is a commercial product G50-medium Sephadex, a molecular sieve based on cross-linked dextran and which is very effective on a column of about 2.5 by 100 centimeters in size. The number "G-50" indicates pore size. From this fractionation step there is collected an extract which has a molecular weight in the range of 4,000–12,000.

The extract is collected since it is partially excluded from the sieve pores and the separation is made by usual chromatographic techniques. The resulting fractions are lyophilized and rerun through the same system, that is, again through the molecular sieves in order to effect as good a separation as possible and obtain only materials having molecular weights in the range of 4,000–12,000. It should be understood of course, that the steps over the molecular sieving may be repeated as many times as necessary or desirable and in fact any of these steps may be repeated in order to enhance purification. According to this invention, it has been found that one repeat of the molecular sieving separation is usually sufficient.

After the fractions are removed from the molecular sieve column and lyophilized they are further fractionated by adsorption chromatography in order to increase purification. Preferably the adsorption chromatography is conducted by dissolving the extract in a 0.001 M to 0.008 M, preferably 0.005 M, phosphate buffer solution at a pH of approximately 6.8 and passing through a column containing hydroxyl apatite. In conducting this step it will be found that the active fractions will be retarded behind the void volume and these are then lyophilized to remove the water, and salt is removed by desalting on a molecular sieve column in which the salts are retained in the pores and the active materials are excluded in the void volume. The principle of this separation by adsorption chromatography is that differential sticking on the hydroxyl apatite is obtained. Thus, in this step the hydroxyl apatite retards the active fraction which is then removed, lyophilized and desalted as indicated.

The resulting material is then fractionated further by ion exchange chromatography preferably using an ion exchanger in which the beads form the backbone and contains active groups thereon. A molecular sieve exchanger of the commercially available Sephadex brand sold as QAE-Sephadex by Pharmacia is admirably suited for this purpose. In this chromatographic step, the material is fractionated on the column in a solution of a buffer base of about 0.5 to 1.5 Molar such as 0.1 M ammonium bicarbonate and preferably at a pH of about 10–11. Additional base such as alkali metal hydroxide or ammonium hydroxide may be added to obtain the desired pH. The extract passes through the column but the active Thymin materials desired are retained by the beads. Thereafter, the column is developed with a linear concentration gradient to 0.8 M ammonium bicarbonate which has also been brought to a pH of about 10–11. This means that while the fractionation was conducted at a molar concentration of about 0.1, raising the molarity from 0.1 M to 0.8 M in accordance with known linear concentration gradients, results in removal of the active material which had been retained by the beads. The resulting products are then lyophilized and desalted on a Sephadex column in 0.1 M ammonium bicarbonate as described above and the resulting lyophilized void volume of these columns constitute the purified Thymins. If these fractions were still impure on analysis by polyacrylamide disc electrophoresis, the ion exchange chromatography step can be repeated until purification is obtained.

The yields from this process vary somewhat from batch to batch but on the average, 1 kilogram of wet thymus will initially yield about 500 milligrams of lyophilized powder after the molecular exclusion chromatography steps, and after the hydroxyl apatite absorption chromatography step, about 50 milligrams will be obtained. Finally, about 1 milligram of each Thymin will be obtained from the final purification steps. In this procedure, the term "lyophilized" means that the mixture is treated by freezedrying to remove water and volatile buffers.

The resulting Thymopoietin products are in the form of a powder and separation is achieved in the column by ion exchange chromatography and fractions containing the materials are identified by measuring the peaks of each of the materials. In FIG. 3, the peaks of Thymin I (Thymopoietin I) and Thymin II (Thymopoietin II) were measured by ultraviolet absorbence but these peaks may be measured by other known methods such as by the Lowry Test and the like as the step being carried out here is merely to measure the concentration of material eluted, in this case, Thymin I (Thymopoietin I) and Thymin II (Thymopoietin II).

As pointed out above, the polypeptides of this invention are therapeutically useful in the treatment of humans and animals. Thus, they have been shown to have a statistically significant effect on neuromuscular transmission. Thymin I (Thymopoietin I) is slightly more active than Thymin II (Thymopoietin II). Thus, since the polypeptides affect neuromuscular transmission and have the capability for inducing the differentiation of lymphopoietic stem cells originating in the hemopoietic tissues to mature thymus derived cells or T cells which are capable of involvement in the immune response to the body, the proucts of this invention are considered to have multiple therapeutic uses. Primarily, since the compounds have the capability of carrying out certain of the indicated functions of the thymus they have application in various thymic function and immunity areas. A primary field of application is in the treatment of DiGeorge Syndrome, a condition in which there is a congenital absence of thymus. Injection of these polypeptides will overcome this deficiency. Because of their biological characteristics, the polypeptides, which are extremely active at low concentrations, are considered useful in assisting the collective immunity of the body in that the polypeptides increase or assist in therapeutic stimulation of cellular immunity and thereby become useful in the treatment of diseases involving chronic infection in vivo, such as fungal or mycoplasma infections, tuberculosis, leprosy, acute and chronic viral infections and the like. Further, Thymin I and Thymin II are considered to be useful in any area in which cellular immunity is an issue and particularly where there are deficiencies in immunity such as in the DiGeorge Syndrome mentioned above. Also where there is an excess of antibody production due to unbalanced T cells and B cells, the polypeptides can correct this condition by stimulating T cell production. Thus, they may be of therapeutic use in certain autoimmune diseases in which damaging antibodies are present, for example, systemic lupus erythematosus. Further, because of the characteristics of the products, they have in vitro usefulness in inducing the development of surface antigens of T cells, in inducing the development of the functional capacity to achieve responsiveness to mitogens and antigens and cell collaborativity in enhancing the ability of B cells to produce antibodies. The polypeptides are also useful in inhibiting the uncontrolled proliferation of thymin-responsive lymphocytes.

An important characteristic of the polypeptides is their in vivo ability to restore cells with the characteristic of the T cells. Therefore, the Thymin I and Thymin II are active in many areas as a result of their ability to enhance the immune response in the body.

A further important property of the Thymin I and Thymin II of this invention is that they are highly active in very low concentrations. Thus, it has been found that the Thymins are active in concentrations ranging from 20 picogram per mll, and are maximally active at concentrations from about 0.2–2 nanogram per mll. The carrier may be any of the well known carriers for this purpose including normal saline solutions, preferably with a protein diluent such as bovine serum albumin to prevent adsorptive losses to glassware at these low concentrations. The Thymin I (Thymopoietin I) and Thymin II (Thymopoietin II) are active at a range of above about 0.1 mg/kg of body weight. For the treatment of DiGeorge Syndrome, the polypeptides may be administered at a rate of about 0.1 to 10 mg/kg of body weight. Generally, the same dosage amounts may be used in treatment of the other conditions or diseases mentioned.

As indicated above, an interpretation of the findings in myasthenia gravis as suggestive of autoimmune thymitis led to the development of a model of the disease in laboratory animals, experimental autoimmune thymitis. Experimental analysis of this model implicated a substance released from the diseased thymus in the pathogenesis of the neuromuscular lesion and experiments on thymectomized and thymus grafted animals indicated that this substance was also secreted by the normal thymus. The prime function of the thymus is the differentiation of lymphopoietic stem cells originating in the haemopoietic tissues to mature thymus-derived cells (T cells) capable of involvement in the immune response of the body. Since this differentiating function is likely mediated by a hormone secreted by the epithelial cells of the thymus, the finding of a hormone affecting neuromuscular transmission raises two possibilities. The thymus may secrete two separate hormone systems, one differentiating lymphopoietic stem cells, the other affecting neuromuscular transmission. Alternatively, by virtue of some similarity in the receptors of lymphopoietic stem cells and the neuromuscular synapse, the one hormone may affect both.

It was found that the peptides of this invention, in subnanogram concentration, caused a detectable neuromuscular lesion and also induced the differentiation of bone marrow cells in vitro in that they acquired antigens characteristic of intrathymic T cells. Thus, these findings suggest that the peptides are primarily hormones of the thymus which induce differentiation of lymphopoietic stem cells and that the effect on neuromuscular transmission is secondary and may be related to the presence of some receptor in the synaptic apparatus which is similar to that of the stem cells. Cholinergic receptors are present on both stem cells and mature lymphocytes, and it is possible that the receptors of stem cells which induce differentiation to T cells may have evolved from such cholinergic receptors.

By this reasoning the neuromuscular effect is a chance one, rather than a primary physiological regulating function in the body. Nevertheless, the mode of action of the peptides in producing the neuromuscular block is of great importance. While thymin results in a post synaptic block in neuromuscular transmission, the evidence is that it does not combine directly with the classical acetylcholine receptor since it is inactive in vitro, causing neither acute blocking nor depolarization, and it has an 18 hour latent period in vivo, the effect then persisting for several days. These findings would suggest that Thymin is affecting a regulatory mechanism in the neuromuscular synapse and Thymin may be a valuable tool for probing such a mechanism of chronic modulation of synaptic conductivity. Furthermore, Thymin I and Thymin II are of therapeutic use in decreasing neuromuscular transmission in conditions where it is excessive, for example spasticity, in that they can be used deliberately to produce partial neuromuscular block and prevent the excessive neuromuscular discharge that occurs in these diseases.

To determine the neuromuscular action of Thymin I and Thymin II, the electromyographic response of mice five days after various doses of Thymin I or Thymin II is summarized in FIG. 4. Bovine serum albumin (0.5 mg/ml, 0.9% saline) was used as a protein stabilizer and controls were injected with the solvent alone.

The chart in FIG. 4 shows the electromyographic response of mice to supramaximal nerve stimulation at a rate of 50 impulses per second. In 15 control mice sampled at 75 sites the height of the tenth muscle action potential was $94 \pm 2\%$ (mean $\pm$ s.e.m.) of the height of the first. The mean values and s.e.m. (vertical bars) are shown for groups of 4–10 mice given various doses of Thymin I(o) and Thymin II (□). Statistical significances of differences from the controls were calculated by Student's t-test and are shown by solid symbols ($P < 0.001$), half solid symbols ($0.05 > P < 0.001$) and open symbols ($P > 0.05$). Most doses of Thymin I above 4 ng/mouse and Thymin II above 32 ng/mouse produced a statistically significant ($P < .001$) decrement (means 84% for Thymin I, 82% for Thymin II) which did not increase with increasing dose above threshold.

The chart in FIG. 5 shows the electromyographic response of mice at various times after a single injection of 100 ng Thymin I expressed as a percentage of the response of mice injected with solvent alone. Mice were given 100 ng of Thymin I or solvent and five mice from each group were tested at various times. With supramaximal nerve stimulation at 50 impulses per second the height of the tenth muscle action potential was expressed as a percentage of the first. This change was calculated for five points in each of five to ten mice from each group. For each time point the change in Thymin-treated mice was expressed as a percentage of the change in solvent-treated control mice and the statistical significance of the difference was assessed by Student's t-test. A statistically significant ($P < .001$) abnormality in the electromyogram was first evident at 18 hours, was maximal at 24 hours and persisted through 5 days.

To make the determinations described in FIGS. 4 and 5, extracts were injected into test animals and neuromuscular transmission was studied after an interval of one to five days. Initially 100 g guinea pigs were injected intraperitoneally; neuromuscular transmission was studied in vitro with a preparation of the phrenic nerve and hemidiaphragm. Subsequently, 200 g rats were used; fractions were injected subcutaneously and neuromuscular transmission was assessed electromyographically. Finally, mice were found to be the most effective test system. Female Swiss-Webster mice weighing 25–35 g were injected intraperitoneally, groups of five to ten mice being used to test each fraction. The animals were anesthetized with urethane and electromyography was performed as described. The muscle action potentials were recorded in each mouse following supramaximal nerve stimulation with ten impulses at a rate of 50 per second. Five sites were sampled in each mouse and for each group of mice the mean standard deviation and s.e.m. were calculated for the change in the height of the muscle action, potential being expressed as a percentage of the height of the first impulse.

Since this response in normal mice was found to vary somewhat with age and size, appropriate controls from the same group of mice were always tested. The statistical significance of differences found were assessed by student's t-test.

The following examples are presented to illustrate the invention but it is not to be considered as limited thereto. In these examples and throughout the specification, parts are by weight unless otherwise indicated.

EXAMPLE 1

ISOLATION OF THYMIN I AND THYMIN II

Bovine thymus was obtained fresh on wet ice, dissected clean and stored at −20° C. Batches were homogenized 25% wet weight/volume in 0.1 M ammonium bicarbonate using a Waring blender. The extract was heated to 70° C. for 30 minutes in a water bath and then centrifuged at 5,000 g for 30 minutes. The supernatant was filtered through gauze and cotton and 0.1% thimerosal was added as a bacteriostatic agent since the subsequent steps were carried out at room temperature. Diaflo membranes (Amicon) and molecular sieve chromatography on Sephadex (Pharmacia) were then used to obtain an enrichment on the basis of molecular size. The extract was processed through a Diaflow XM100A (pore size) membrane in a TC10 apparatus, a thin layer dialyzer (Amicon). The dialysate was then concentrated over a Diaflow UM2 membrane, using a 402 cell pressurized to 55 psi; 2 liters were concentrated to 15 ml. This retentate was further fractionated by molecular exclusion chromatography on a 2.5×100 cm column of G-50 medium Sephadex (Pharmacia) in 0.1 M ammonium bicarbonate. The outflow was monitored with a Uvicord I monitor (LKB) which recorded ultraviolet transmittance at 254 nm. The fractions were lyophilized and rerun on the same column.

The lyophilized fractions from G-50 Sepadex were fractionated by adsorption chromatography on hydroxy apatite (Biorad). A 500 mg load was dissolved in 0.005 M sodium phosphate buffer, pH 6.8, and applied on a 2.5×30 cm column of hydroxyl apatite in the same buffer. Active fractions were found retarded behind the void volume and they were lyophilized and desalted on a G-25 Sephadex column. This material was fractionated further by ion exchange chromatography on a 1.5×30 cm column of QAE-Sephadex (Pharmacia) in 0.1 M ammonium bicarbonate brought to pH 10.5 with ammonium hydroxide. The column was developed with a linear concentration gradient to 0.8 M ammonium bicarbonate, also brought to pH 10.5. The two fractions obtained are shown in FIG. 3 and were active in producing neuromuscular block. These were designated Thymin II and Thymin I and each was lyophilized and desalted on G-25 Sephadex in 0.1 M ammonium bicarbonate, the lyophilized void volume of these columns constituted the purified thymins. If these fractions were still impure on analysis by polyacrylamide disc electrophoresis, the ion exchange chromatography step was repeated.

The yields varied somewhat from batch to batch; on the average one kg of wet thymus yielded 500 mg of lyophilized powder after the Sephadex G-50 steps, this yielded 50 mg after hydroxyl apatite adsorption chromatography and the final yield was approximately 1 mg of each thymin in powder form.

The electromyographic assay was adaquate to detect peaks of activity during fractionation. However, due to the eventual finding of two polypeptides with slightly different thresholds of action and due to the wide variations in normal electromyographic responses which required large numbers of test animals and controls to assess variations statistically, it was not possible to quantitate enrichments and yields of activity for each step of the isolation.

EXAMPLE 2

The following examples show that the purified Thymins induce the expression of serologically defined thymic antigens in spleen and bone marrow cells at subanogram concentrations.

MATERIALS AND METHODS

Animals

Mice of the A/J, C57B1/6J, AKR/J and C58/J strains were purchased from the Jackson Laboratories (Bar Harbon, Me). A.TL-mice were bred at New York University from foundation stock. All mice were housed eight to a cage, and maintained on commercial high protein mouse pellets and acidified water.

Antisera

Antibodies to TL antigen were produced by injecting live tumor cells (ASL-1) into A.TL- x C57B1/6J F.1 mice. After five semimonthly injections the animals were bled and the resultant serum pooled, absorbed with A.TL- thymus to remove autoantibodies, and stored in small aliquots at −70° C. The serum pool used in these experiments had a cytotoxic titre of 1:2,500 when titrated against ASL-1. Anti Thy 1-2 (0-C3H) was produced by injecting AKR/J mice with C58/J thymocytes and absorbing the resultant antiserum with AKR/J thymocytes. The serum pool used had a cytotoxic titer of 1:400 when tested against ASL-1.

Thymin

Thymin I and Thymin II were isolated from bovine thymus as described. Each was dissolved in phosphate buffered saline (containing 1 mg/ml of bovine serum albumen to minimize adsorbtive losses), distributed into 2 μg lots and lyophilized. Each polypeptide was reconstituted in tissue culture medium at the desired concentrations just prior to use.

Induction of thymic antigens

Bone marrow cells were obtained from the femoral marrow. Both spleen and marrow cells were teased into single cell suspensions and washed three times in RPMI 1640 medium supplemented with 10 mM Hepes and 100 U/ml of penicillin and 100 μg/ml of streptomycin. The cells were then suspended in the same medium with 10% bovine serum at a concentration of $5.0\times10^6$ cells/ml. One milliliter of this suspension was incubated with an appropriate dilution of thymin in 16 mm plastic petrie dishes in a humidified atmosphere containing 5% $CO_2$ in air. At the end of the incubation the cells were washed twice and held at 4° C. at a concentration of $5.0\times10^6$ cells/ml in culture medium until tested for the presence of TL or Thy-1(0).

Target cells

ASL-1, a TL positive, Thy 1-2 (0-C3H) positive lymphoma of A strain mice was used as the target cell in all titrations of the antisera used in these experiments, and in the cytotoxic inhibition test to be described below. The lymphoma was maintained by weekly intraperitoneal passage in A/J mice. Lymophoma cells were labelled with $Cr^{51}$ and used as target cells in the cytotoxic inhibited test.

Cytotoxic inhibition test

Antisera to either TL or Thy-1 (0) were titered to determine the quantity of antibody which was required to kill 50% of the target cells in a standard suspension. The appropriate amount of antiserum was added to each well of a microtiter plate with various dilutions of the cells being tested for their antigen content. The total volume was 0.15 ml. Cells expressing the antigen against which the antiserum was directed absorbed varying amounts of the antibody, and rendered less available to react with the $Cr^{51}$ labelled target cells which were added subsequently. The concentration of antibody used was extremely critical to the sensitivity of the test. The antisera to TL or Thy-1 (0) and the cells being tested for their antigen content were incubated together at 4° C. for 90 minutes. After this incubation 50,000 target cells in a volume of 0.25 ml were added and the incubation continued in the cold for an additional 30 minutes to permit the sensitization of the target cells by the remaining unabsorbed antibody. The plates were then centrifuged at 1,500 rpm for 10 minutes and the supernatant fluid removed. The pelleted cells were resuspended in 0.1 ml or RPMI 1640, containing 4% fresh rabbit serum as a source of complement, and incubated for 45 minutes at 37° C. The cells were then repelleted by centrifugation and a 0.075 ml aliquot of the supernatant fluid was counted in an automatic gamma spectrometer to determine the amount of $Cr^{51}$ released from the target cells. All assays were performed in duplicate and the results were expressed by calculating the number of cells required to reduce the relative cytotoxic index (RCI) to 0.5. The RCI was calculated as follows:

$$RCI = \frac{\text{CPM released in the presence of absorbing cells} - \text{CPM released without antibody}}{\text{CPM released in the absence of absorbing cells} - \text{CPM released without antibody}}$$

Direct Cytotoxic Test

Bone marrow and spleen cells were obtained by flotation in BSA gradients similar to those used by Komuro and Boyse (*Lancet,* 10, 39, 1964). These cells were tested for their susceptibility to anti TL and Thy-1-(0) antibodies in a direct cytotoxicity test, using the uptake of trypan blue as a measure of cell death.

TEST RESULTS

Induction of TL and Thy-1(θ)

Figure 6:
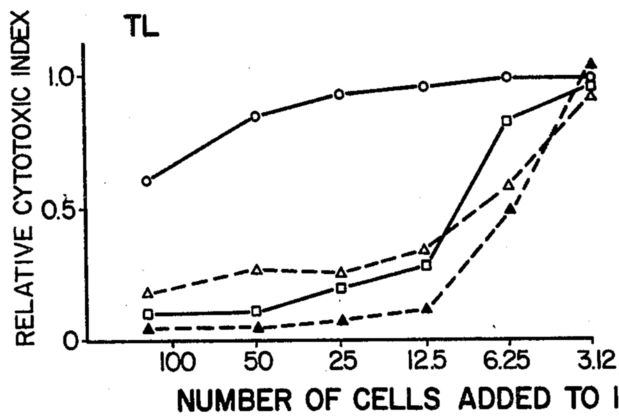
FIG. 6 is a graph showing the absorption of anti TL and anti Thy-1($\theta$) antibody by bone marrow cells incubated with Thymin I and Thymin II.
Figure 6:
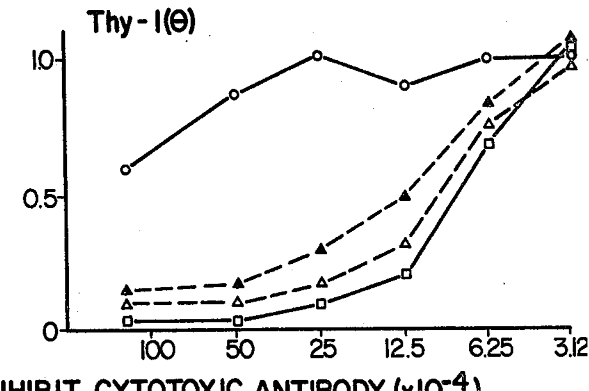

FIG. 6 shows the results of a cytotoxic inhibition test in which the induction of both TL and Thy-1(θ) antigens on mouse bone marrow cells was demonstrated. In this experiment unfractionated cells were incubated with 100 ng/ml of Thymin I or Thymin II for 18 hours. At the end of this time these cells absorbed antibodies directed against either TL or Thy-1(θ). Cells incubated under similar conditions without thymin remained unable to absorb these antibodies. The relative amount of antigen which these cells expressed could be estimated by comparing the number of cells from each culture and the number of normal TL positive thymocytes required to produce a reduction of the relative cytotoxic index (RCI) to 0.5. Bone marrow cells cultured with thymin express 50% more TL and 30% less Thy-1(θ) than normal thymocytes.

The actual number of cells induced could not be determined in the cytotoxic inhibition assay since this test is a measure of the total antigen present in the culture. The direct cytotoxic test does indicate the actual number of cells which have acquired sufficient antigen to be lysed by antiserum and complement. However, unless sufficient numbers of such cells are present they cannot be detected because of a substantial background usually found in such tests. Thus, TL induction could not be detected in unfractionated cells by the direct cytotoxic test, but when bone marrow or spleen cells were fractionated by flotation on discontinuous bovine serum albumen gradients, significant induction could be demonstrated in the least dense fractions of both tissues. Thus, in this experiment, after incubation with 20 ng/ml of Thymin I for two hours, anti TL antiserum plus complement caused the death of 18% of the spleen and 21% of the bone marrow cells. Values as high as 28% were obtained in other experiments. Bone marrow cells from genetically TL negative mice did not acquire TL antigen after incubation with thymin, nor did bone marrow cells from TL positive mice when similarly incubated with thymin at 4° C.

Figure 7:
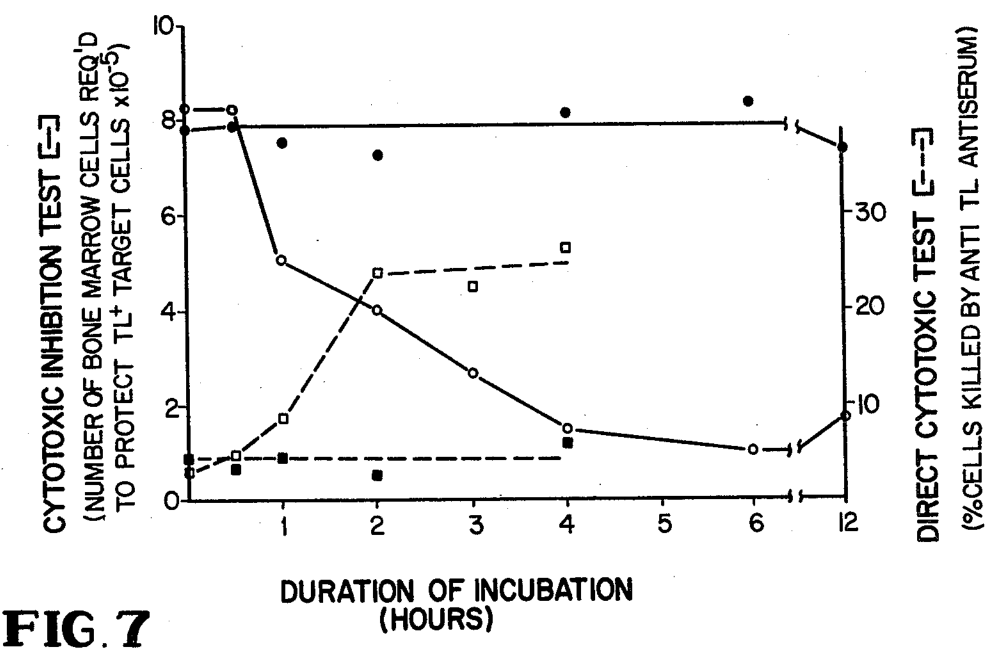
FIG. 7 is a graph showing the kinetics of the appearance of TL antigen on bone marrow cells incubated with Thymin I.

Time course of the induction:

FIG. 7 indicates the kinetics of the appearance of TL antigen on bone marrow cells incubated with Thymin (20 mg/ml). The results using both the cytotoxic inhibition test and the direct cytotoxicity test are shown. In the former, unfractionated bone marrow was used, while in the latter only cells from the least dense fraction of the BSA density gradients were used. TL antigen was detected in both tests after one hour of incubation. In the direct cytotoxicity test the maximum number of cells sensitive to anti TL antibody and complement was reached after two hours. At this time almost one quarter of the cells in the low density fraction were susceptible to cytolysis by anti TL antisera. Further incubation did not increase the proportion of susceptible cells. The quantitiy of TL expressed by these cells, as measured in the cytotoxic inhibition test, continued to increase for four hours. This is indicated in FIG. 7 by the decreasing number of cells required to protect the $Cr^{51}$ labelled target cells from lysis by anti TL antibody and complement.

Dose response

Figure 8:
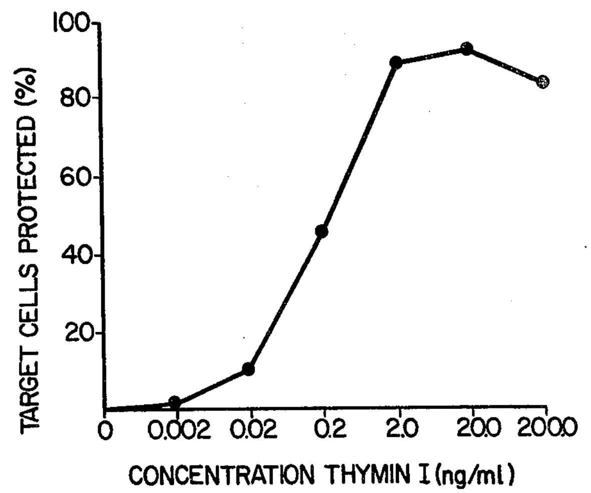
FIG. 8 is a graph showing the relationship between the concentration of Thymin I and the amount of TL antigen induced thereby.

The Thymins were extremely potent in inducing the appearance of TL and Thy-1($\theta$) antigens. Maximal induction was achieved with 2 ng/ml of Thymin I and as little as 20 pg/ml produced a measurable response. A representative dose response for the induction of TL antigen by Thymin I is shown in FIG. 8. Thymin I was generally slightly more potent than Thymin II.

It has been demonstrated that bone marrow cells rapidly acquired characteristic thymic differentiation antigens (TL and Thy-1($\theta$) when incubated in the presence of low concentrations of the purified polypeptides Thymin I and Thymin II. The concentration at which the Thymins acted was within the range usually found with other polypeptide hormones and the lowest detectable concentration (20 pg/ml) represented only several hundred molecules per susceptible cell. No other putative thymic factor has approached this level of activity. The most potent preparation previously reported was that of Bach et al., (Proc. Acad. Sci., 68, 2734, 1971) which was said to be minimally active at a concentration of between 10 and 100 ng per $3\times10^6$ bone marrow cells. Thymin I is active at approximately one thousandth this concentration.

The quantity of TL and Thy-1($\theta$) detected on bone marrow cells treated with optimal amounts of thymin was remarkably high. Although only 5–10% of the cells in the thymin treated marrow expressed sufficient TL to become susceptible to immune cytolysis with anti-TL antiserum, the total amount of TL in the cultures was 50% greater than that found in an equivalent number of thymocytes. This indicated that the bone marrow cells expressing TL actually had 15–25 times more of the antigen than average normal thymocytes. Similarly these cells had 6–12 times more Thy-1($\theta$) than average normal thymocytes. These findings would be consistent with the known events associated with thymoctye maturation. TL disappears from thymocytes while they are still within the thymus and the amounts of Thy-1($\theta$) in peripheral "T" lymphocytes is much reduced compared to that on intrathymic thymocytes. It appears that the highest concentration of these antigens occurs in the earliest phases of thymocyte differentiation, and that they are progressively diminished on each cell as it matures. They thymin induced cells, on which was demonstrated such high amounts of TL and Thy-1($\theta$), would thus correspond to an early stage in thymoctye maturation.

A surprising finding in earlier studies of induction using partially purified thymus extracts was the rapidity of onset of differentiation, and the short period of time over which maximum numbers of differentiated cells appeared. These findings were reported by Komuro and Boyse (*Lancet,* 1, 740, 1973) using direct cytotoxic assay to measure TL and Thy-1($\theta$) expression, and by Bach et al (Proc. Acad. Sci. 68, 2734, 1971), using the development of azathioprine sensitive rosette forming cells. The results herein using the direct cytotoxic test to measure TL expression were in general agreement, but parallel studies using the cytotoxic inhibition test suggested that this suddenness of appearance of differentiation may have been related to the tests used. Reactive cells rather than antigen quantity are measured in these tests. Until a sufficient density of antigen appears on the cell surface, the cells resist cytolysis or rosette formation. Once the critical concentration of antigen is achieved, the tests become positive, and no further changes can be detected. By the indirect cytotoxic test there was detected a progressive increase of TL antigen over four hours. It is believed that this reflects more accurately the changes occurring at the cell surface.

The invention has been described herein with reference to certain preferred embodiments. However, as obvious variations thereon will become apparent to those skilled in the art, the invention is not to be considered as limited thereto.

What is claimed is:

1. A highly purified polypeptide named as Thymopoietin I and having the following amino acid sequence:

$H_2N$-GLY-GLN-PHE-LEU-GLU-ASP-PRO-SER-VAL-LEU-THR-LYS-GLU- LYS-LEU-LYS-SER-GLU-LEU-VAL-ALA-ASN-ASN-VAL-THR-LEU-PRO-ALA-GLY-GLU- GLN-ARG-LYS-ASP-VAL-TYR-VAL-GLN-LEU-TYR-LEU-GLN-HIS-LEU-THR-ALA-VAL- LYS-ARG-COOH, said polypeptide existing in the physical form of a powder, said polypeptide having relative mobilities on 7% polyacrylamide disc electrophoresis of 0.3 at a pH of 8.9 with respect to bromophenol blue, and 0.63 at a pH of 4.3 with respect to methyl green, said polypeptide being therapeutically active at concentrations of 0.2-2 nanogram per ml.

2. A highly purified polypeptide named as Thymopoietin II and having the following amino acid sequence:

$H_2N$-SER-GLN-PHE-LEU-GLU-ASP-PRO-SER-VAL-LEU-THR-LYS-GLU- LYS-LEU-LYS-SER-GLU-LEU-VAL-ALA-ASN-ASN-VAL-THR-LEU-PRO-ALA-GLY-GLU- GLN-ARG-LYS-ASP-VAL-TYR-VAL-GLN-LEU-TYR-LEU-GLN-THR-LEU-THR-ALA-VAL- LYS-ARG-COOH, said polypeptide existing in the physical form of a powder, said polypeptide having relative mobilities on 7% polyacrylamide disc electrophoresis of 0.3 at a pH of 8.9 with respect to bromophenol blue, and 0.57 at a pH of 4.3 with respect to methyl green, said polypeptide being therapeutically active at concentrations of 0.2–2 nanogram per ml.

3. A method for the isolation from bovine thymus of the polypeptides Thymopoietin I and Thymopoietin II, which comprises homogenizing bovine thymus in buffered saline solution, heating to a temperature of about 60°–90° C. to complete homogenization, centrifuging and filtering to remove non-homogenized and insoluble materials and provide a resulting solution, subjecting this resulting solution to molecular sizing by contacting with a dialysate membrane of such size as to allow polypeptides to pass through the membrane while excluding materials having molecular weights above about 100,000, passing the resulting solution which passed through the membrane through a second dialysate membrane of such size so as to exclude materials having molecular weights below about 2,000, recovering therefrom a retentate containing materials having molecular weights of about 2,000–100,000 and of reduced volume, fractionating the resulting retentate by molecular exclusion chromatography at least two times by placing in a solution of ammonium bicarbonate and contacting the solution with a cross-linked dextran molecular sieve which totally excludes materials having molecular weights above about 30,000 wherein materials having molecular weights of less than about 1500 will totally permeable and recovering an extract containing materials having molecular weights in the range of about 4,000 to about 12,000, further fractionating the resulting extract by adsorption chromatography by dissolving the extract in a solution 0.001 M to 0.008 M phosphate buffer solution at a pH of about 6.8 and contacting with hydroxy apatite by passage through a column containing the hydroxyl apatite, and separation is effected by differential sticking on the hydroxyl apatite, the active fractions being retarded behind the void volume, collecting the active fractions by lyophilizing and desalting, fractionating to separate two active fractions by contact at least once by ion exchange chromatography by dissolving in a buffer base at a pH of about 10 to 11 and contacting with an anion exchanger comprising beads as the backbone with polymer groups attached thereon wherein the product is retained by the beads, recovering the product fractions by raising the molarity of the solution by linear concentration gradients, lyophilizing and desalting the resulting active fractions on a cross-linked dextran molecular sieve and recovering the purified Thymopoietin I and Thymopoietin II.

4. A method according to claim 3 wherein the bovine thymus is homogenized in about 25% wet weight per volume of 0.1 M ammonium bicarbonate.

5. A method according to claim 4 wherein heating is carried out at a temperature of about 70° C. for 30 minutes.

6. A method according to claim 5 wherein the homogenized mixture is centrifuged after heating at 5,000 g for 30 minutes to remove non-homogenized materials.

7. A method according to claim 6 wherein the retentate from the second dialysis step is fractionated by molecular exclusion chromatography in a solution of 0.1 M ammonium bicarbonate.

8. A method according to claim 7 wherein the recovered materials from the second dialysis step are fractionated by ion exchange chromatography in the presence of an anion exchanger in 0.1 M ammonium bicarbonate and is later removed by raising the molarity of the solution to 0.8 M by linear concentration gradients.

* * * * *